United States Patent [19]

Maser

[11] Patent Number: 5,520,925
[45] Date of Patent: May 28, 1996

[54] MATERIAL ON THE BASIS OF COLLAGEN FIBERS FOR COVERING WOUNDS

[75] Inventor: Franz Maser, Mannheim, Germany

[73] Assignee: Naturin GmbH & Co., Weinheim, Germany

[21] Appl. No.: 211,867

[22] PCT Filed: Aug. 20, 1993

[86] PCT No.: PCT/EP93/02239

§ 371 Date: Oct. 24, 1994

§ 102(e) Date: Oct. 24, 1994

[87] PCT Pub. No.: WO94/04201

PCT Pub. Date: Mar. 3, 1994

[30] Foreign Application Priority Data

Aug. 21, 1992 [DE] Germany .......................... 42 27 681.0

[51] Int. Cl.⁶ ........................................................ A61K 9/70
[52] U.S. Cl. ............................................. 424/443; 424/445
[58] Field of Search ........................................ 424/443, 445

[56] References Cited

U.S. PATENT DOCUMENTS

| | | | |
|---|---|---|---|
| 4,925,924 | 5/1990 | Silver | 530/356 |
| 5,028,695 | 7/1991 | Eckmayer | 530/356 |

FOREIGN PATENT DOCUMENTS

| | | |
|---|---|---|
| 0331786 | 9/1989 | European Pat. Off. . |
| 2734503 | 1/1979 | Germany . |
| 2730623 | 9/1979 | Germany . |
| 2943520 | 4/1981 | Germany . |
| 2079797 | 1/1982 | United Kingdom . |

*Primary Examiner*—D. Gabrielle Phelan
*Attorney, Agent, or Firm*—Cushman Darby & Cushman

[57] ABSTRACT

A foil-shaped wound covering material based on collagen fibers, its laminates, and a process for preparing the same are disclosed. The wound covering material essentially consists of insoluble, partially modified collagen characterized by the following parameters: 0.18 to 0.40 mmol/g amidated nitrogen; less than 5 μmol/g glucosamine and less than 5 μmol g galactosamine; shrinking temperature from 45° to 60° C.; isoelectric point from 4.3 to 60.0.

16 Claims, No Drawings

MATERIAL ON THE BASIS OF COLLAGEN FIBERS FOR COVERING WOUNDS

This application is a 371 of PCT/EP93/02239, filed Aug. 20, 1993.

FIELD OF THE INVENTION

The invention relates to material in foil form on the basis of collagen fibers for covering wounds.

BACKGROUND OF THE INVENTION

Skin transplants are often required in connection with many injuries and also in connection with surgical operations, but suitable skin from the injured themselves or others is not always available. It has therefore been attempted for a long time to cover particularly large wound areas, such as burn injuries, with other materials in order to prevent the loss of fluids and external infections. Experiments in this field have been performed for some years with "artificial skin" on the basis of collagen fibers. The results obtained with such a type of "artificial skin" have been mixed so far.

The long-fiber, linear-colloid, scleroproteins of the extracellular matrix which, together with proteoglycan, appear in connective tissue, in the protein-containing basic substance of bones and in dentine, are called collagen. Depending on their origin, the composition of the proteins can vary, various types of collagens are known which, however, not all have a fiber structure. The small proportion of tryptophan, tyrosin and cystine in collagens is remarkable, but collagens are distinguished by a large proportion of glycine, prolin and in particular 4-hydroxy-prolin. Collagens are first synthesized in fibroblasts, i.e. cells of the connective tissue, in the form of procollagen chains of a molecular weight of approximately 140,000. Hydroxylation of prolin and lysine under the influence of ascorbic acid and glycolization only take place in the chain, after which three chains then combine in the form of levo-rotated helices which in turn are dextroverted around each other. This substance then is excreted in the extracellular space, in which peptides are split off the ends of the chains, so that so-called tropocollagen is created, which combines into fibrils. While the tropocollagen is still salt- or acid-soluble, collagen fibrils are insoluble. The tropocollagen of a molecular weight of approximately 300,000 consists of three polypeptide chains which may have a slightly different amino acid sequence. As a rule, two chains are identical, the third has a different structure.

In contrast to most proteins of the human or animal body, collagens are not continuously renewed, instead they have a long biological half-life which may be up to 300 days. The collagens are quite resistant to enzymatic decomposition, essentially, the enzymatic decomposition of native collagens can only be achieved by means of collagenase. The soluble fission products being created following the proteolysis of the collagen fibrils are hydrolized by other proteases into peptides and amino acids.

Soluble as well as insoluble collagens have already been experimentally used as "artificial skin". Corresponding products have been described, for example, in Japanese Patent Application 59 160464 or in U.S. Pat. No. 4,600,533. The material has also been suggested for endoprotheses, for example the European Patent Application 85 200045. An "artificial skin" of this type reduces fluid loss and protects against external infection, in addition, this type of artificial skin is intended to have an inflammation-reducing and hemostatic effect and to increase the growth of epithelic cells. The collagens used as the raw material up to now are soluble collagens as a rule because of easier processing. This has the disadvantage that the membranes or films have relatively only little stability because they consist of non-fibrous collagens which to not natively occur in this form. In addition, the collagen used continues to be enzymatically dissolved. Up to now, these membranes or films were made of collagen gels, which were produced in accordance with various techniques, known per se, and were then converted into solid form. Corresponding products are described, for example, in U.S. Pat. Nos. 4,600,533, 4,689,399 or 4,725, 641 and 4,294,241. In accordance with U.S. Pat. No. 3,800, 792, an attempt was made to improve the lack of stability in that the sponge structure produced from a collagen gel was linked and provided with a plastic film, however, this clearly worsened the adaptation and adherence of the material to the wound. The fact that, as already mentioned, the adherence of these films to the wound is not very pronounced when used as a dressing, is a disadvantage of all collagen films known up to now, so that as a rule additional fixation of the edges is required, particularly, if large areas must be covered. A further difficulty with the materials known up to now consists in that they can be decomposed relatively quickly and that, as a result of their processing, they still have a considerable proteoglycan content, which can lead to allergic reactions which as a rule are slight, but may be markedly pronounced in individual cases, because this is, after all, a material which is alien to the body and not human. In addition, it is not very easy to maintain products made of soluble collagen sterile and to make them capable of storage, because the decomposition or further decomposition of the amino acid chains cannot be completely disrupted. When producing films or membranes of insoluble collagen, however, there is always the difficulty of cleaning the fibers of extraneous material, such as the allergy-creating proteoglycans, to the extent that a quite safe use, in particular on large areas of the body, is possible. A combination of a collagen film of soluble collagen with hyaluronic acid is already known from Japanese Patent Application 61 041462. Hyaluronic acid comprises the basic components of D-glycuronic acid and N-acetyl-D-glucosamine in a 1,3-glycosidic bond and can have molecular weights between approximately 50,000 and several million, depending on its origin and processing. Hyaluronic acid can bond to fibrins and together with them forms a three-dimensional matrix, by means of which the original fibrin matrix is deformed, swells and becomes porous. Faster and improved infiltration and migration of cells into the matrix is made possible because of this. Hyaluronic acid has an intense stimulating effect on the speed of formation of fibrin matrices which were induced by thrombin. Thus the hyaluronic acid content in the wound increases shortly after the injury and, in addition to cell infiltration and swelling of the matrix, the substance also affects the phagocytosis and vascularization of newly formed tissue. Therefore hyaluronic acid plays a very essential role in the building, conversion and decomposition of the fibrin matrix, so that its addition to collagen films is desirable, because the hyaluronic acid ensures faster healing of the wound with less complications.

However, the "artificial skins on a collagen basis" known up to now still have the disadvantages of not displaying good adherence, being able to trigger immune reactions and allergies and not being particularly inexpensive. In addition, the permeability to water is great and the decomposition too fast. Therefore there is still a need for further wound covering materials on the basis of collagen fibers which do not have these disadvantages.

SUMMARY OF THE INVENTION

In accordance with the invention a wound covering material in foil form and based on collagen fibers is now proposed which is distinguished in that it consists of insoluble, partially modified collagen, which is different from native collagen particularly by the following parameters, namely amide nitrogen, glucosamine and galactosamine content, isoelectric point and shrinking temperature.

Surprisingly it has now been found that it is possible to obtain a substance by partial modification of native, insoluble collagen which is extremely well suited for producing films which are usable as a dressing material. The modification is performed by means of a gentle hydrolysis, wherein the portion of the amide groups of asparagine and glutamine in particular are reduced and in this way the isoelectric point is displaced. In addition, splitting of crosslinking of the natural fibrils takes place, but the fibrillar structure of the native insoluble collagen remains intact. The gentle hydrolysis can be performed in different ways, known to one skilled in the art in the protein field.

DETAILED DESCRIPTION OF THE INVENTION

In accordance with the invention, cowhide strips are allowed to swell in acid in accordance with the conditioning method known to one skilled in the art from German Patent DE-PS 659 940. The dry matter content of collagen rinds pre-processed in this way is approximately 16.0% by weight, the amide nitrogen content lies at approximately 0.28 mmol/gr of dry mass, the ash content comes to approximately 0.4% by weight (referring to the dry mass), and the pH value is 2.8 to 2.9. These pre-treated rinds are then pre-comminuted in a suitable manner. The mass of rind is then placed into ice and water and this suspension is additionally mixed with glycerin and sorbitol or other physiologically harmless means for keeping it moist. If desired, it is also possible to add a physiologically harmless organic or inorganic tanning agent in this process stage. The suspension is stirred in the mixing vessel and is carefully mixed; the pH value is again adjusted to approximately 2.8 to 2.9 with hydrochloric acid. The particles of this suspension are then further comminuted in a manner known per se, so that at the end a gel-like swelled dispersion, which macroscopically appears to be homogeneous, with a pH value of approximately 2.8 and a dry collagen content of 2% is obtained. This dispersion is subsequently extruded as a foil in a manner known per se. The still moist foil is neutralized to a physiologically acceptable range, preferably pH 5, for example by treatment with ammonia gas. Prior to rolling it up, the foil is conditioned by again increasing the water content to approximately 12 to 18, preferably approximately 15 percent by weight, and it can then be packaged and stored or used. The material manufactured in this manner can be sterilized and, as far as tests up to now have shown, can be stored almost indefinitely, because practically no chemical reactions occur even after extended storage.

If the foil is to be combined with hyaluronic acid, the latter is either already added in suitable concentration when the suspension is prepared, or it is subsequently layered on the finished film after extrusion. However, in place of hyaluronic acid, other substances which positively affect the healing of the wound can also be added, such as antibiotics, substances which aid in cell growth, hemostatic compounds or adhesion factors. As in the case of the hyaluronic acid, they are worked in either in the course of preparing the suspension or by later application to the extruded foil.

The wound covering material of the invention is distinguished in that, in comparison to the initial material, amide nitrogen, the glucosamine and galactosamine content, the isoelectric point and the shrinking temperature are clearly changed. With an initial material of fresh beef skin, the following values are obtained on the average:

Shrinking temperature 68° C.

Amide nitrogen 0.52 mmol/g

Isoelectric point 7.0 to 7.8

In comparison therewith, the basic collagen modified in accordance with the invention has the following values:

Shrinking temperature 45° to 60° C.

Amide nitrogen 018–0.40 mmol/g

Isoelectric point 4.3 to 6.0

Glucosamine and galactosamine: each less than 6 µmol/g.

The collagen foils of the invention are clearly more tear-resistant than the collagen membranes so far manufactured in accordance with the prior art, and they exhibit an adherence not attained up to now, because in the moist state they are particularly resilient and conforming, by means of which good coverage of even irregular or uneven wounds is made possible and as a rule an edge fixation is no longer required. If required, it is also possible to place several layers on top of each other, without adherence being negatively affected. The foils are hydrophilic, so that moisture and gases can penetrate and can be carried away from the wound, while at the same time the material forms a protection against exogenous microorganisms. The foils display hemostatic and pain-killing properties and can be easily and painlessly removed, so that there is no unnecessary stress on the patient when checking the wound or changing the bandage. It is also of particular importance that the foils of the invention to not have any allergic effects, so that no reactions need to be anticipated, even with sensitive or predisposed patients. Incidentally, the material is completely absorbed and decomposes in the body, without any immunological problems being noted in this area even in complicated cases.

A further advantage lies in that the initial material can be manufactured in large amounts and that the production costs of the foil are relative low, compared to the methods usual up to now, so that the cost allows a larger use than before.

Incidentally, it has been found that for special uses it can be particularly desirable to employ the foil of the invention in the form of a laminate. In these cases the collagen foil can either be laminated with occluding films on the basis of, for example, polyesters, polymethylmetacrylates, polyurethanes or polyetherurethanes, or with films of foamed materials, such as polyurethane foam or sponge-like structures on the basis of, for example, collagen or hydrocolloids. Laminates with planar textile structures, such as gauze, fleece materials of different types, or gauze bandages can be of great usefulness on special occasions. Production of such laminates by calendering, gluing with physiologically harmless adhesives or in other ways is known to one skilled in the art. It is also possible to metallize the foils of the invention by applying thin layers of aluminum, copper or silver in a manner known per se. The technology of metallizing foils is known to one skilled in the art. Foils metallized in this manner are distinguished by a very low permeability of water vapor, which is desirable in some cases. When employing oligodynamically acting metal, such as copper or silver, a bactericidal effect can additionally be achieved.

The invention will be described in more detail below by means of examples:

EXAMPLE 1

Collagen rinds swelled in acid in accordance with a conditioning method known to one skilled in the art, for example from German Patent DE-PS 659 940, are prepared from cowhide strips. The dry matter content is 10.0% by weight, the amide nitrogen content lies at approximately 0.28 mol/gr of dry mass, the ash content comes to 0.4% by weight (referring to the dry mass), and the pH value is 2.0.

These collagen rinds are then coarsely pre-comminuted in a manner known to one skilled in the art.

45 kg of the resulting raw mass are mixed in an appropriate mixing vessel with 80 kg of ice, 212.5 l of water, 1.8 l of glycerin (84 percent by weight), 0.4 l of sorbitol (70 percent by weight) and 0.2 kg $Al_2(SO_4)_3 \times 18H_2O$. All components are stirred in the mixing vessel and carefully mixed. The pH value is adjusted to 2.8 by means of hydrochloric acid.

On the basis of this mixture, a macroscopically homogeneous-appearing, ventilated, gel-like swelled dispersion with a pH value of 2.8 and a dry collagen content of 2.0% is obtained, which subsequently is extruded onto an endless conveyor belt through a slot die.

The conveyor belt passes through a drying tunnel. Prior to the end of the drying process, the foil is treated with ammonia gas until the pH value of the finished foil lies around 5. After drying, the foil is reconditioned by raising its water content to approximately 15 weight percent and is cut and packaged.

EXAMPLE 2

To manufacture a collagen foil containing hyaluronic acid, the process of Example 1 is used, but with the following addition: 45 kg of the coarsely pre-comminuted rinds are mixed with 80 kg of ice, 211 l of water, 1.8 l of glycerin (84 percent by weight), 0.4 l of sorbitol (70 percent by weight), 2.0 kg $Al_2(SO_4)3 \times 18H_2O$ and 0.18 kg hyaluronic acid (molecular weight=greater than 500,000), dissolved in 1.2 l of water, and adjusted to a pH value of 2.8 by means of hydrochloric acid. Further processing takes place as described.

I claim:

1. A wound covering material in the form of a foil on the basis of collagen fibers, characterized that it essentially consists of insoluble, partially modified collagen having the following parameters:

hyaluronic acid in the amount of 1% to 8% by weight and water in the amount of 12% to 18% by weight;

amide nitrogen 0.18 to 0.40 mmol/g;

glucosamine and galactosamine: each less than 5 µmol/g;

shrinking temperature 45° to 60° C.

isoelectric point 4.3 to 6.0.

2. A wound covering material as claimed in claim 1 wherein the foil is laminated with a foil of a physiologically harmless plastic material.

3. A wound covering material as claimed in claim 1 wherein said foil is laminated with a foam of spongy structure made from collagen.

4. A wound covering material as claimed in claim 1 wherein said foil is laminated with a planar textile structure.

5. A wound covering material as claimed in claim 1 wherein said foil is laminated with a foil of physiologically harmless metal.

6. The wound covering material as claimed in claim 1 wherein the hyaluronic acid is present in the amount of 2% to 5% by weight.

7. The wound covering material as claimed in claim 1 or 3 wherein the material has a water content of approximately 15% by weight.

8. A wound covering material in accordance with claim 6, characterized in that the hyaluronic acid has a molecular weight greater than 500,000.

9. A wound covering material in accordance with claim 6, characterized in that the material has a water content of approximately 12 to 18, weight-%.

10. A method for producing a wound covering material in the form of a film comprising collagen fibers consisting essentially of insoluble, partially modified collagen having the following parameters:

hyaluronic acid in the amount of 1% to 8% by weight and water in the amount of 12% to 18% by weight;

amide nitrogen in the amount of 0.18 to 0.40 mmol/g;

glucosamine and galactosamine in the amount each less than 5 µmol/g;

a shrinking temperature of between 45° to 60° C.; and an isoelectric point of 4.3 to 6.0, comprising the steps of swelling beef skin in acid, comminuting the beef skin and cooling the beef skin to a temperature below 10° C., mixing the comminuted cooled beef skin with physiologically harmless agents for keeping it moist, homogenizing the beef skin and processing it into a film by extrusion and raising the pH of the extruded film to approximately a physiological medium.

11. A method in accordance with claim 10, characterized in that prior to extruding the suspension is adjusted to a dry mass content of approximately 2 weight-%.

12. A method in accordance with claim 10, characterized in that prior to drying the film is treated with ammonia gas until a pH of approximately 5 has been reached.

13. A method in accordance with claim 10, characterized in that after drying the film is adjusted to a water content of approximately 12 to 18, weight-%.

14. A method in accordance with claim 10, characterized in that prior to homogenizing, 1 to 8, weight-% of hyaluronic acid are added to the suspension and is vigorously mixed.

15. The method as claimed in claim 10 wherein the step of mixing the beef skin with physiologically harmless agents for keeping it moist includes using vegetable tanning agents.

16. The method as claimed in claim 10 wherein the physiologically harmless agent for keeping the beef skin moist is aluminum sulfate hydrate.

* * * * *